(12) United States Patent
Frach et al.

(10) Patent No.: US 8,822,935 B2
(45) Date of Patent: Sep. 2, 2014

(54) METHOD TO IMPROVE THE TIME RESOLUTION OF DIGITAL SILICON PHOTOMULTIPLIERS

(75) Inventors: Thomas Frach, Aachen (DE); Gordian Prescher, Cologne (DE)

(73) Assignee: Koninklijke Philips N.V., Eindhoven (NL)

( * ) Notice: Subject to any disclaimer, the term of this patent is extended or adjusted under 35 U.S.C. 154(b) by 239 days.

(21) Appl. No.: 13/319,107

(22) PCT Filed: Apr. 15, 2010

(86) PCT No.: PCT/IB2010/051647
§ 371 (c)(1),
(2), (4) Date: Nov. 7, 2011

(87) PCT Pub. No.: WO2010/136910
PCT Pub. Date: Dec. 2, 2010

(65) Prior Publication Data
US 2012/0068077 A1    Mar. 22, 2012

Related U.S. Application Data

(60) Provisional application No. 61/181,705, filed on May 28, 2009.

(51) Int. Cl.
| G01T 1/17 | (2006.01) |
| H03K 5/22 | (2006.01) |
| G04F 10/00 | (2006.01) |
| A61B 6/03 | (2006.01) |
| G01T 1/29 | (2006.01) |

(52) U.S. Cl.
CPC ............ G01T 1/2985 (2013.01); H03K 5/22 (2013.01); G04F 10/005 (2013.01); A61B 6/037 (2013.01)

USPC .......................................... 250/369; 327/24

(58) Field of Classification Search
CPC ........ G01T 1/29; G01T 1/2985; G04F 10/005
USPC ..................................... 250/363.02–363.03
See application file for complete search history.

(56) References Cited

U.S. PATENT DOCUMENTS

| 6,754,613 B2 | 6/2004 | Tabatabaei et al. |
| 7,030,382 B2 | 4/2006 | Williams et al. |

(Continued)

FOREIGN PATENT DOCUMENTS

| EP | 1835307 A1 | 9/2007 |
| JP | 2004012279 A | 1/2004 |

(Continued)

OTHER PUBLICATIONS

Swann et al. "100-ps Time-Resolution CMOS Time-to-Digital Converter for Positron Emission Tomography Imaging Applications," IEEE Journal of Solid-State Circuits, vol. 39, No. 11, Nov. 2004: p. 1839-1852.*

(Continued)

*Primary Examiner* — Casey Bryant

(57) ABSTRACT

A radiation detector module (10) for use in a time-of-flight positron emission tomography (TOF-PET) scanner (8) generates a trigger signal indicative of a detected radiation event. A timing circuit (22) including a first time-to-digital converter (TDC) (30) and a second TDC (31) is configured to output a corrected timestamp for the detected radiation event based on a first timestamp determined by the first TDC (30) and a second timestamp determined by the second TDC (31). The first TDC is synchronized to a first reference clock signal (40, 53) and the second TDC is synchronized to a second reference clock signal (42, 54), the first and second reference clock signals being asynchronous.

21 Claims, 4 Drawing Sheets

(56) References Cited

U.S. PATENT DOCUMENTS

| | | |
|---|---|---|
| 7,091,489 B2 | 8/2006 | Schlyer et al. |
| 7,205,924 B2 * | 4/2007 | Vemulapalli et al. ......... 341/166 |
| 7,403,589 B1 * | 7/2008 | Short et al. ...................... 378/19 |
| 7,968,849 B2 | 6/2011 | Ohtani |
| 2004/0056202 A1 * | 3/2004 | Rao .............................. 250/369 |
| 2005/0012033 A1 | 1/2005 | Stern et al. |
| 2007/0278409 A1 * | 12/2007 | Cook et al. ............... 250/363.03 |
| 2008/0203309 A1 * | 8/2008 | Frach et al. ................... 250/362 |
| 2009/0072153 A1 | 3/2009 | Musrock |
| 2009/0153377 A1 * | 6/2009 | Chang ............................ 341/53 |
| 2010/0134335 A1 * | 6/2010 | Park et al. ..................... 341/118 |

FOREIGN PATENT DOCUMENTS

| | | |
|---|---|---|
| WO | 2007146587 A2 | 12/2007 |
| WO | 2009019660 A2 | 2/2009 |

OTHER PUBLICATIONS

Yousif, A. S., et al.; A Fine Resolution TDC Architecture for Next Generation PET Imaging; 2007; IEEE Trans. on Nuclear Science; 54(5)1574-1582.

* cited by examiner

METHOD TO IMPROVE THE TIME RESOLUTION OF DIGITAL SILICON PHOTOMULTIPLIERS

CROSS REFERENCE TO RELATED APPLICATIONS

This application claims the benefit of U.S. provisional application Ser. No. 61/181,705 filed May 28, 2009, which is incorporated herein by reference.

The following relates to the detector arts. It finds particular application in conjunction with radiation detectors for time-of-flight positron emission tomography (TOF-PET) but may also find applicant in other nuclear medical imagers employing radiation transmission or radiopharmaceuticals, such as single photon emission computed tomography (SPECT) imagers and positron emission tomography (PET) imagers as well as planar x-ray imagers, radio-astronomy, detectors for high energy particles (e.g. Cherenkov radiation, synchrotron radiation, colorimetric detectors, etc.), and the like, and will be described with particular reference thereto. It will be appreciated that the invention may also be applicable to other radiation detector modalities, and in systems and methods employing radiation detectors.

In positron emission tomography (PET), a radiopharmaceutical is administered to the imaging subject, in which the radioactive decay events of the radiopharmaceutical produce positrons. Each positron interacts with an electron to produce a positron-electron annihilation event that emits two oppositely directed gamma (γ) rays. Using coincidence detection circuitry, a ring array of radiation detectors surrounding the imaging subject detect the coincident oppositely directed gamma ray events corresponding to the positron-electron annihilation(s). A line of response (LOR) connecting the two coincident detections intersects the position of the positron-electron annihilation event. Such lines of response are analogous to projection data and can be reconstructed to produce a two- or three-dimensional image. In time-of-flight PET (TOF-PET), the small time difference between the detection of the two coincident γ ray events is used to localize the annihilation event along the LOR (line of response).

The performance of PET systems is influenced by sensitivity, time resolution and response, and noise. PET radiation detector modules traditionally include an array of photomultiplier tubes (PMT's) optically coupled with a scintillator crystal using an intermediate light guide layer. Solid state photoelectric detectors such as digital silicon photomultipliers (SiPM) optically coupled to a pixelated scintillator have also been proposed. SiPMs are based on avalanche photodiodes (APDs) operating in the Geiger mode. They are characterized by an improved sensitivity to γ rays and are less sensitive to scattering effects; however, they are prone to dark counts, which do not originate photon absorption.

A time-to-digital convertor (TDC) outputs a timestamp associated with each detected radiation event. The timestamp is used by the coincidence detection circuitry to determine coincidence pairs and the corresponding LORs and by the time-of-flight measurement circuitry. Traditionally, TDCs consist of a coarse counter and a fine counter. The coarse counter is a digital counter configured to count the rising edges of the reference clock. When an event is detected, a switch at the input of the coarse counter is latched into a register as a part of the timestamp. The fine counter measures the time difference between detected event and the subsequent rising edge of the reference clock as the remaining part of the timestamp. The output is a timestamp with a temporal resolution typically less than 100 picoseconds.

However, an event may or may not be detected due to a phenomenon known as meta-stability. Meta-stability is an unstable state that persists for an indefinite period typically occurring in synchronous circuits with one or more asynchronous inputs. A flip-flop is one device that is susceptible to meta-stability under certain conditions. A flip-flop has two logic states, a change at the input causes the flip-flop to alternate between the states. However, if the input changes during the setup or hold times it may enter a meta-stable state between the two logic states. The meta-stable state eventually decays to one of the two logic states, but the decay time can be significant making exact time measurements difficult.

In the example of a TDC, the input is connected to a flip-flop that is latched in response to a detection signal generated by a photoelectric detector. If the detection signal occurs during a rising edge of the reference clock and as a result the flip-flop enters a meta-stable state, the event is not detected until the next rising edge of the reference clock. Meta-stability at the input of the TDC can seriously affect the precision of the timestamp, thus reducing the accuracy of coincidence detection which can introduce significant noise into images.

The solid state nature of SiPMs allows for the integration of digital TDCs close to the APDs, thus improving the timing resolution of the PET system. Flip-flops with shorter setup and hold times have been proposed; however, traditional TDCs implementations still suffer from meta-stability because of the circuit design.

The present application provides a new and improved timing circuit suitable for PET detectors or other electronics which overcomes the above-referenced problems and others.

In accordance with one aspect, a timing circuit with a first and second TDC is presented. The first TDC is configured to output a first timestamp based on a first reference clock signal, and the second TDC is configured to output a second timestamp based on a second reference clock signal. A circuit outputs a corrected timestamp based on the first and second timestamp.

In accordance with another aspect, a method for assigning a timestamp is presented. A first and second reference clock signals are generated, in which the reference clock signals are non-synchronous. A trigger signal is received in response to a detected event. A first timestamp is determined based on a temporal relationship between the trigger signal and the first reference clock signal, and a second timestamp is determined based on a temporal relationship between the trigger signal and the second reference clock signal. A corrected timestamp is outputted based on the first and the second timestamps.

One advantage is that time resolution of timing circuits are improved.

Another advantage resides in redundancy.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 diagrammatically shows a medical imaging system employing radiation detector modules with pixilated scintillator;

FIG. 2 diagrammatically shows the timing circuit of FIG. 1;

Figure 1:
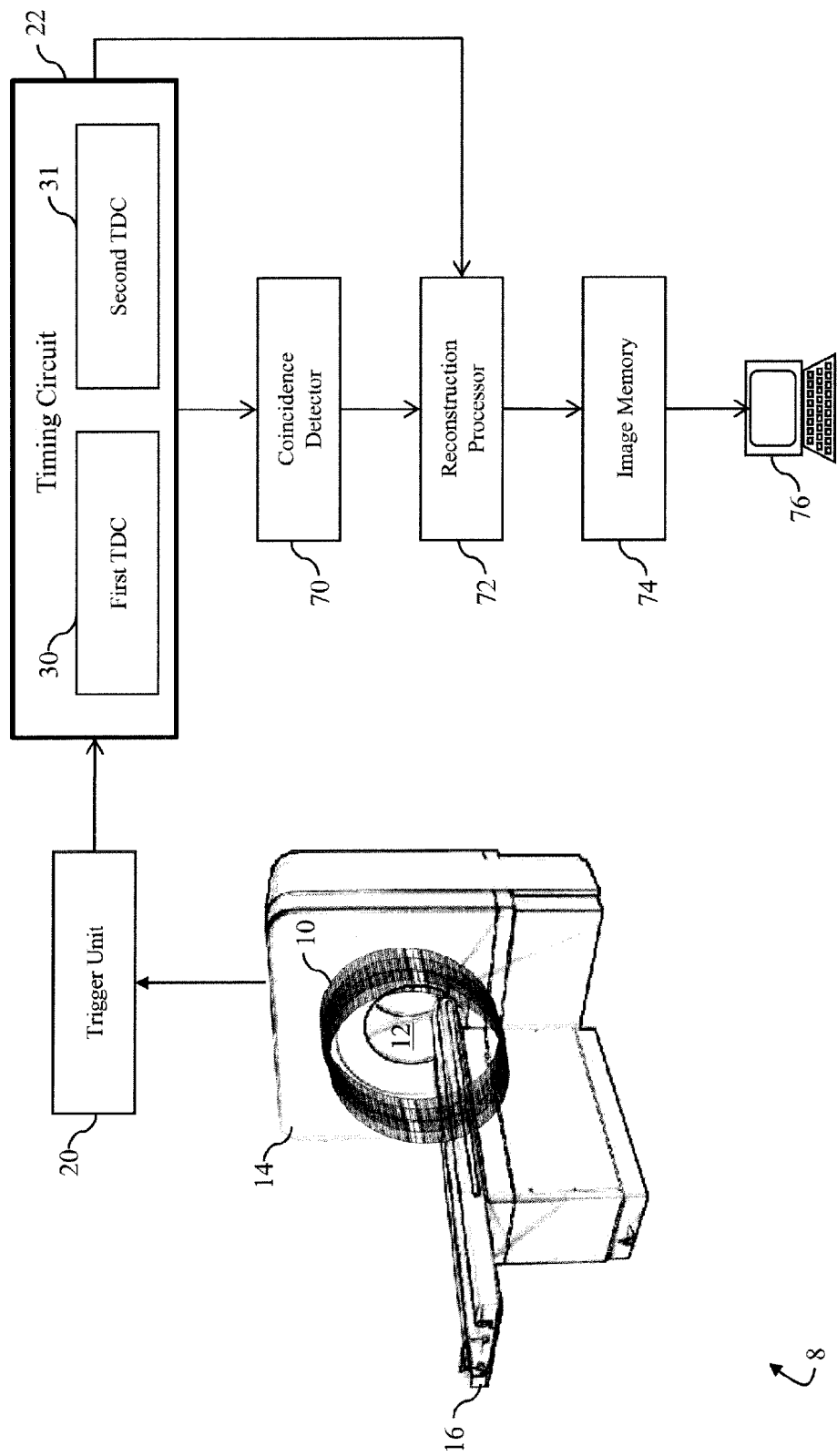

With reference to FIG. 1, a radiation tomography scanner 8 is described as an illustrative example. More generally, the timing circuit disclosed herein can be practiced in substantially any signal processing application that generates a digital representation of time indices for a plurality of stochastic signal pulses. For example, the timing circuitry can be used in conjunction mass spectrometry, high energy particle physics, radio-astronomy, medical imaging, or the like where the signal pulses represent a detected event.

The radiation tomography scanner 8 includes a plurality of radiation detector modules 10 oriented to receive radiation from an imaging region 12. The radiation detector modules 10 are arranged in several adjacent rings along an axial direction; however, other arrangements of radiation detector modules can be used. Typically the radiation detector modules 10 are housed within a housing 14 of the tomography scanner 8 and thus are not visible from the outside. Each ring is comprised of hundreds or thousands of radiation detector modules 10. In some scanners, only a single ring of radiation detector modules 10 is provided, in others, up to five or more rings of radiation detector modules 10 are provided. It should be appreciated that detector heads can be used in place of the detector ring structure shown in FIG. 1. The tomography scanner 8 includes a subject support 16 for positioning an object or patient in the imaging region 12. Optionally, the support 16 is linearly movable in the axial direction generally transverse to the rings of the radiation detector modules 10 to facilitate acquisition of three-dimensional imaging data over an extended axial distance.

Each radiation detector module 10 typically includes a scintillator crystal disposed adjacent to the examination region. The scintillator crystal absorbs the γ ray (e.g. 511 keV in PET scanners) to generate a scintillation of optical photons. The photons are detected at the opposite end of the scintillator crystal by an array of photoelectric detectors such as photomultiplier tubes, photodiodes, SiPMs, or the like. In another embodiment, the scintillator crystal is a pixelated scintillator constructed from a plurality of optically isolated scintillator crystals, each coupled to a single photoelectric detector. Upon detection of photons, the photoelectric detector outputs a signal, or a plurality of signals if multiple photoelectric detectors are viewing the scintillation event, that is indicative of a detected radiation event. Each photoelectric detector is operatively connected to a trigger unit 20 that monitors the photoelectric detector output for the signal. If a signal is detected the trigger unit generates a trigger signal for the timing circuit 22, so as to timestamp the detected radiation event.

Figure 2:
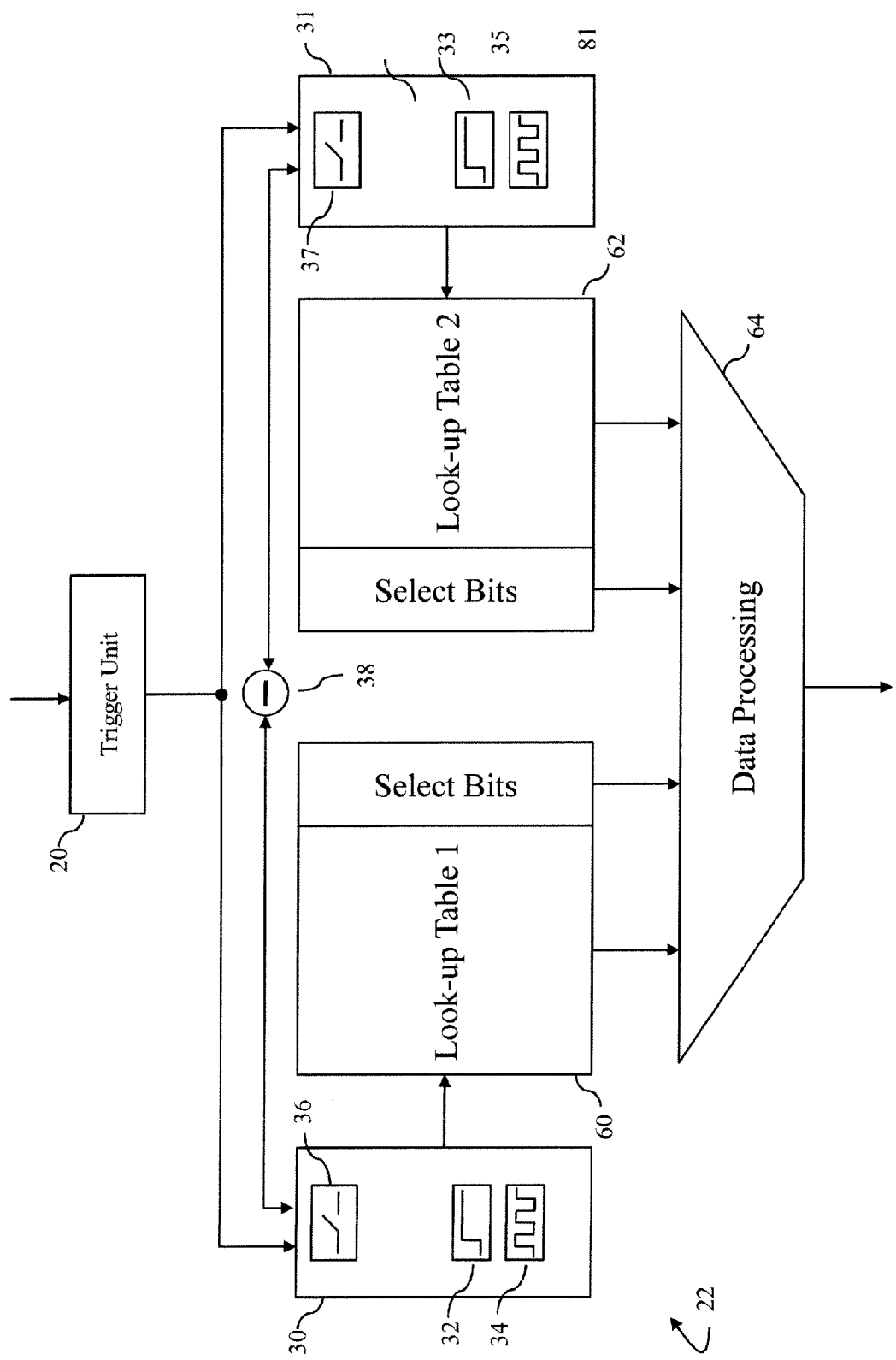

With reference to FIG. 2, the timing circuit 22 includes at least two time-to-digital converters (TDCs) 30, 31; each receives the same input from the trigger unit 20. Each TDC consists of a coarse counter 32, 33 and a fine counter 34, 35. The coarse counter is a digital counter configured to count the rising edges of the reference clock, and the fine counter measures the time difference between detected event and the subsequent rising edge of the reference clock as the remaining part of the timestamp. The time difference measurement performed by the fine counter is based on a time-to-distance measurement according to one of tap line, a Vernier, a pulse-shrinking, and a constant current capacitor discharge, or the like.

At the input of each TDC, a storage element 36, 37, e.g. a flip-flop, latch, or the like, is latched when the trigger signal is present. If the input is stable the switch will latch at the subsequent rising edge of the reference clock. However, if the trigger signal is received at the input during a meta-stable region, i.e. during the setup or hold times, the switch may become meta-stable and the trigger signal will not be latched until the next rising edge of the reference clock leading to a significant increase in the timestamp error.

To reduce timing errors stemming from meta- stability at the input each TDC is synchronized to a unique reference clock. The first TDC 30 is synchronized to a first reference signal and the second TDC 31 is synchronized to a second reference signal. In one embodiment (FIG. 3), the rising edge of the first reference signal corresponds to the falling edge of the second reference signal and vice versa so that the reference signals are negated versions of one another. In another embodiment (FIG. 4), while maintaining the same rate of oscillation, the two reference signals are shifted with respect to one another. In this manner, a detected radiation event is measured by each TDC separately, thus providing two independent time stamps related to the complementary clocks. As both counters are running on the same (negated or shifted) clock frequency, their values must correspond before the rising edge of the first reference clock signal. A comparator 38 can be used to detect any differences, e.g. due to electromagnetic interference, a radiation event, or the like, and initiate a system synchronization or reset.

Figure 3:
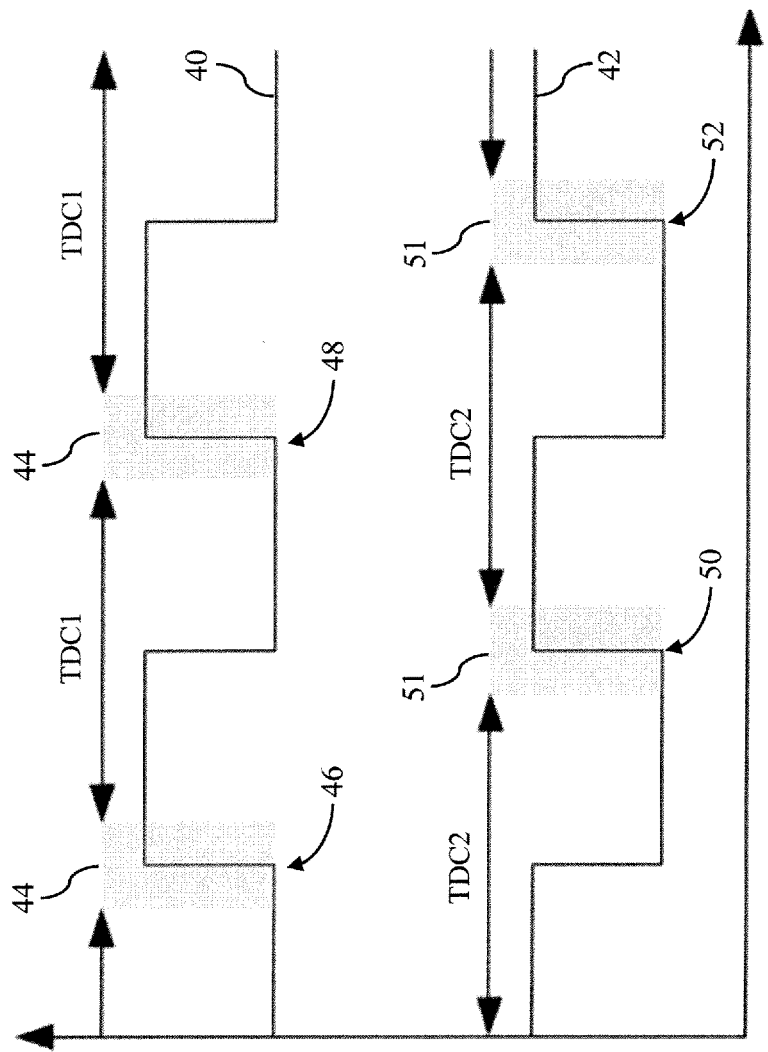
FIG. 3 is a timing diagram of one embodiment of the timing circuit.

FIG. 3 depicts a timing diagram that relates a first reference signal 40 to a negated second reference signal 42. If a detected radiation event occurs during a meta-stable region 44 of the first TDC 30 at time 46, an entire cycle TDC1 will elapse until the timestamp can be captured at the next rising edge at time 48 which can be on the order of a few nanoseconds. Since the input will be stable before the subsequent rising edge of the second reference signal 42, the second TDC 31 will capture the detected radiation event at time 50, thus reducing the timestamp error. Conversely, if the detected radiation event occurs during a meta-stable region 51 of the second TDC, the first TDC will capture the timestamp at time 48 instead of time 52, an entire cycle TDC2 later. As both counters are running on the same (positive and negated) clock, their values must be identical before the rising edge of the positive clock. A comparator can be used to detect any differences, e.g. due to electromagnetic interference, a radiation event, or the like, and initiate a system synchronization or reset.

Figure 4:
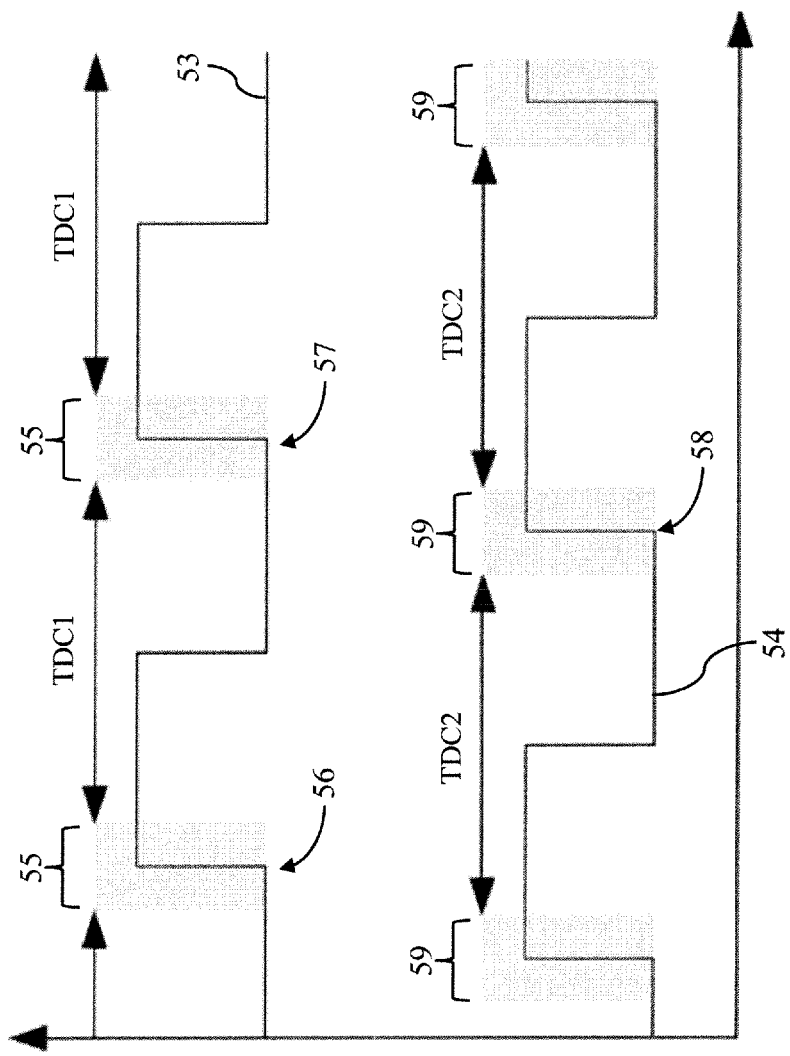
FIG. 4 is a timing diagram of another embodiment of the timing circuit.

FIG. 4 depicts a timing diagram that relates a first reference signal 53 to a shifted second reference signal 54. If a detected radiation event occurs during a meta-stable region 55 of the first TDC 30 at time 56, an entire cycle TDC1 will elapse until the timestamp can be captured at the next rising edge at time 57 which can be on the order of a few nanoseconds. Since the input will be stable before the subsequent rising edge of the second reference signal, the second TDC 31 will capture the detected radiation event at time 58, thus reducing the timestamp error. Conversely, if the detected radiation event occurs during meta-stable 59 at time 58 of the second TDC, the first TDC will capture the timestamp at time 57 instead of an entire cycle TDC2 later.

With reference again to FIG. 2, in the event that both timestamps for a single detected radiation event are valid, a circuit such as a look up table 60, 62 along with a data processing unit 64 determines which TDC should be used for a given timestamp. Alternatively, the timestamps can be correlated using the statistical mean or another mathematical/statistical relationship. Optionally, the processing unit can disable unreliable events/bins to improve yield and allow for consistent signal degradation over time. Issues regarding signal degradation are prevalent in nuclear medicine in which a significant radiation dose is detected.

With reference again to FIG. 1, a patient on the support 16 is injected with a radiopharmaceutical. Radiation events are detected by the radiation detector modules 10. A corrected time stamp is associated with each sensed scintillation event by the timing circuit 22. A coincidence detector 70 determines coincident pairs from the timestamps applied by the timing circuit 22 and the LOR defined by each coincident pair. A reconstruction processor 72 reconstructs the LORs into an image representation which is stored in an image memory 76. In a TOF-PET system, the reconstruction processor also localizes each event by deriving time-of-flight information from the timestamps for each LOR. The more precise the timestamp the more accurately each event can be localized along its LOR. A graphic user interface or display device 58 includes a user input device which a clinician can use to select scanning sequences and protocols, display image data, and the like. It should also be appreciated that additional, greater than the two described, TDCs can be implemented into the timing circuit 22 to improve redundancy and improve timing resolution.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A timing circuit, comprising:
   a first time-to-digital converter (TDC) configured to output a first timestamp in response to a detected event based on a first reference clock signal;
   at least a second TDC configured to output a second timestamp in response to said detected event based on a second reference clock signal, the at least first and second reference clock signals being temporally offset; and
   a circuit operatively connected to each TDC configured to output a corrected timestamp based on the earliest of the first and second timestamps.

2. The timing circuit according to claim 1, wherein
   the first reference clock signal and the second reference clock signal oscillate at the same frequency; and
   a rising edge of the first reference clock signal does not coincide with a rising edge of the second reference clock signal and does not coincide with a fading edge of the second reference clock signal.

3. The timing circuit according to claim 1, each TDC further including:
   a coarse counter configured to count a number of rising edges of the corresponding reference clock signal; and
   a fine counter, operating at a higher resolution than the corresponding reference clock, configured to measure a time difference between the detected event and the next rising edge of the corresponding reference clock.

4. The timing circuit according to claim 3, wherein the time difference measurement performed by the fine counter is based on a time-to-distance measurement.

5. The timing circuit according to claim 3, wherein each coarse counter further includes:
   a storage element configured to latch the detected event and the rising edge of the reference clock.

6. The timing circuit according to claim 3, further including a comparator configured to detect differences between the fine counter of both the first and second TDC.

7. A radiation detector module, comprising:
   a scintillator which generates optical photons in response to received radiation;
   a plurality of photoelectric detectors optically coupled to the scintillator configured to generate a trigger signal in response to detected photons; and
   a timing circuit according to claim 1.

8. The radiation detector module according to claim 7, wherein the photoelectric detectors include silicon photomultipliers.

9. The radiation detector module according to claim 7, wherein:
   the scintillator is a pixelated scintillator constructed of a plurality of optically isolated scintillator crystals; and
   each photoelectric detector is optically coupled to one of the scintillator crystals.

10. A nuclear medical image scanner, comprising:
    a plurality of the radiation detection modules according to claim 7, geometrically arranged about an imaging region;
    a coincidence detector which detects pairs of detected radiation events and determines lines of response corresponding to the coincident pairs; and
    a reconstruction processor which reconstructs the lines of response into an image representation.

11. The timing circuit according to claim 1, wherein
    the first TDC associates a time stamp to a detected event unless the detected event occurs during a metastable phase of the first TDC; and
    when the detected event occurs during the metastable phase of the first TDC, the second TDC associates the time stamp to the detected event.

12. A timing circuit
    comprising:
    a first time-to-digital converter (TDC) configured to output a first timestamp in response to a detected event based on a first reference clock signal, the first TDC including:
       a first coarse counter configured to count a number of rising edges of the first reference clock signal following each detected event, the first coarse counter passing through a metastable state during each rising edge such that for an event occurring during the metastable state, the rising edge during the event is not counted; and
       a first fine counter, operating at a higher resolution than the first reference clock, configured to measure a time difference between the detected event and the next rising edge of the first reference clock;
    at least a second TDC configured to output a second timestamp in response to said detected event based on a second reference clock signal, the at least first and second reference clock signals being temporally offset, the second TDC including:
       a second coarse counter configured to count a number of rising edges of the second reference clock signal following each detected event, the second coarse counter passing through a metastable state during each rising edge such that for an event occurring during the metastable state, the rising edge during the event is not counted; and
       a second fine counter, operating at a higher resolution than the second reference clock, configured to measure a time difference between the detected event and the next rising edge of the second reference clock;
    an output circuit operatively connected to the first TDC and the second TDC, when the event is detected by both the first TDC and the second TDC, then the output circuit is configured to output a corrected timestamp is based on the earliest of the first timestamp and the second timestamp.

13. The timing circuit according to claim 12, wherein each coarse counter further includes:
a storage element configured to latch the detected event and the rising edge of the reference clock.

14. The timing circuit according to claim 12, wherein
the first TDC associates a time stamp to a detected event unless the detected event occurs during a metastable phase of the first TDC; and
when the detected event occurs during the metastable phase of the first TDC, the second TDC associates the time stamp to the detected event.

15. A radiation detector module, comprising:
a pixelated scintillator constructed of a plurality of optically isolated scintillator crystals wherein the pixelated scintillator generates optical photons in response to received radiation;
a plurality of silicon photomultipliers photoelectric detectors optically coupled to the pixelated scintillator configured to generate a trigger signal in response to detected photons; and
the timing circuit according to claim 12.

16. A method for assigning a timestamp to a detected event, including:
generating a first reference clock signal;
generating at least a second reference clock signal, the at least first reference clock signal and the second reference clock signal being non-synchronous;
receiving a trigger signal in response to a detected event;
determining a first timestamp based on a temporal relationship between the trigger signal and the first reference clock;
determining at least a second timestamp based on a temporal relationship between the trigger signal and at least the second reference clock; and
outputting a corrected timestamp based on at least the first timestamp and the second timestamp wherein
the first reference signal and the second reference signals oscillate at the same frequency; and
a rising edge of the first reference clock signal does not coincide with a rising edge of the second reference clock signal and does not coincide with a falling edge of the second reference clock signal.

17. The method according to claim 16, further including:
determining the first timestamp;
counting a number of rising edges of the first reference clock signal;
measuring a time difference between the detected event and the next rising edge of the corresponding reference clock with a higher resolution that the first reference clock signal; and
determining the second timestamp;
counting a number of rising edges of the second reference clock signal;
measuring a time difference between the detected event and the next rising edge of the second reference clock with a higher resolution that the second reference clock signal.

18. The method according to claim 17, wherein the time difference measurement is based on a time-to-distance measurement according to one of tap line or a Vernier, or other methods like pulse-shrinking or constant current capacitor discharge.

19. An imaging method, including:
detecting radiation events;
assigning a timestamp according to the method of claim 16 to each radiation event;
from the timestamps, matching pairs of coincident radiation events;
defining an LOR to each pair of coincident radiation events;
reconstructing the LORs into an image representation.

20. The method according to claim 19, further including:
from the timestamps of coincident pairs, localizing the detected radiation event along the LOR defined by the coincident pair.

21. The method according to claim 16, wherein in response to the first reference clock being in a metastable state, determining the first time stamp based on the second reference clock.

* * * * *